(12) United States Patent
Weidner

(10) Patent No.: US 10,672,517 B2
(45) Date of Patent: Jun. 2, 2020

(54) METHOD AND DEVICE FOR MONITORING A BREAST EXAMINATION

(71) Applicant: SIEMENS HEALTHCARE GMBH, Erlangen (DE)

(72) Inventor: Tom Weidner, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 22 days.

(21) Appl. No.: 15/599,698

(22) Filed: May 19, 2017

(65) Prior Publication Data

US 2017/0337336 A1 Nov. 23, 2017

(30) Foreign Application Priority Data

May 19, 2016 (DE) .................. 10 2016 208 647

(51) Int. Cl.
*G16H 50/20* (2018.01)
*A61B 6/00* (2006.01)
*A61B 6/02* (2006.01)
*A61B 5/103* (2006.01)
*A61B 8/08* (2006.01)
*A61B 6/04* (2006.01)
*G06T 7/00* (2017.01)
*G06F 19/00* (2018.01)

(52) U.S. Cl.
CPC ............. *G16H 50/20* (2018.01); *A61B 5/103* (2013.01); *A61B 6/025* (2013.01); *A61B 6/463* (2013.01); *A61B 6/502* (2013.01); *A61B 8/0825* (2013.01); *G06F 19/321* (2013.01); *G06T 7/0012* (2013.01); *A61B 6/0414* (2013.01); *A61B 6/466* (2013.01); *G06T 2207/30068* (2013.01)

(58) Field of Classification Search
CPC ... G06F 19/345; G06F 19/321; A61B 8/0825; A61B 5/103; G16H 50/20; G06T 7/0012; G06T 2207/30068
See application file for complete search history.

(56) References Cited

U.S. PATENT DOCUMENTS

| 7,698,152 B2 | 4/2010 | Reid |
| 8,326,012 B2 | 12/2012 | Kreeger et al. |
| 9,042,612 B2 | 5/2015 | Gkanatsios et al. |
| 9,361,711 B2 * | 6/2016 | Jerebko ................ G06T 11/006 |
| 2006/0155579 A1 * | 7/2006 | Reid ..................... G06F 19/321 |
| | | 705/2 |

(Continued)

FOREIGN PATENT DOCUMENTS

| DE | 102006000713 A1 | 7/2006 |
| DE | 102011052842 A1 | 2/2012 |

(Continued)

*Primary Examiner* — Pinalben Patel
(74) *Attorney, Agent, or Firm* — Laurence Greenberg; Werner Stemer; Ralph Locher

(57) ABSTRACT

A method for monitoring a breast tissue examination is described. In the method, a completed diagnostic assessment of individual image slices of a slice image dataset to be examined in respect of breast tissue that is to be examined is registered automatically. In addition, information relating to the already assessed and the not yet assessed image slices is displayed to a user. An examination workflow monitoring device is also described. A diagnostic assessment station is described in addition.

15 Claims, 3 Drawing Sheets

(56) References Cited

U.S. PATENT DOCUMENTS

| | | | | |
|---|---|---|---|---|
| 2007/0078674 A1* | 4/2007 | Weinberg | ............. | G06F 19/321 |
| | | | | 715/817 |
| 2010/0086188 A1* | 4/2010 | Ruth | ................... | G06K 9/4638 |
| | | | | 382/131 |
| 2010/0306328 A1* | 12/2010 | Amberg | ............... | G06F 19/321 |
| | | | | 709/206 |
| 2012/0045111 A1* | 2/2012 | Palma | ................... | G06T 7/0012 |
| | | | | 382/132 |
| 2013/0028374 A1* | 1/2013 | Gkanatsios | ............ | A61B 6/025 |
| | | | | 378/37 |
| 2016/0051215 A1* | 2/2016 | Chen | ..................... | A61B 6/025 |
| | | | | 715/771 |
| 2016/0110584 A1* | 4/2016 | Remiszewski | ........ | G06T 7/0012 |
| | | | | 382/133 |
| 2016/0283657 A1* | 9/2016 | Bhotika | ................ | G06F 19/321 |
| 2017/0173262 A1* | 6/2017 | Veltz | ................... | A61M 5/1723 |

FOREIGN PATENT DOCUMENTS

| | | |
|---|---|---|
| DE | 202007019608 U1 | 5/2014 |
| EP | 2535829 A2 | 12/2012 |

\* cited by examiner

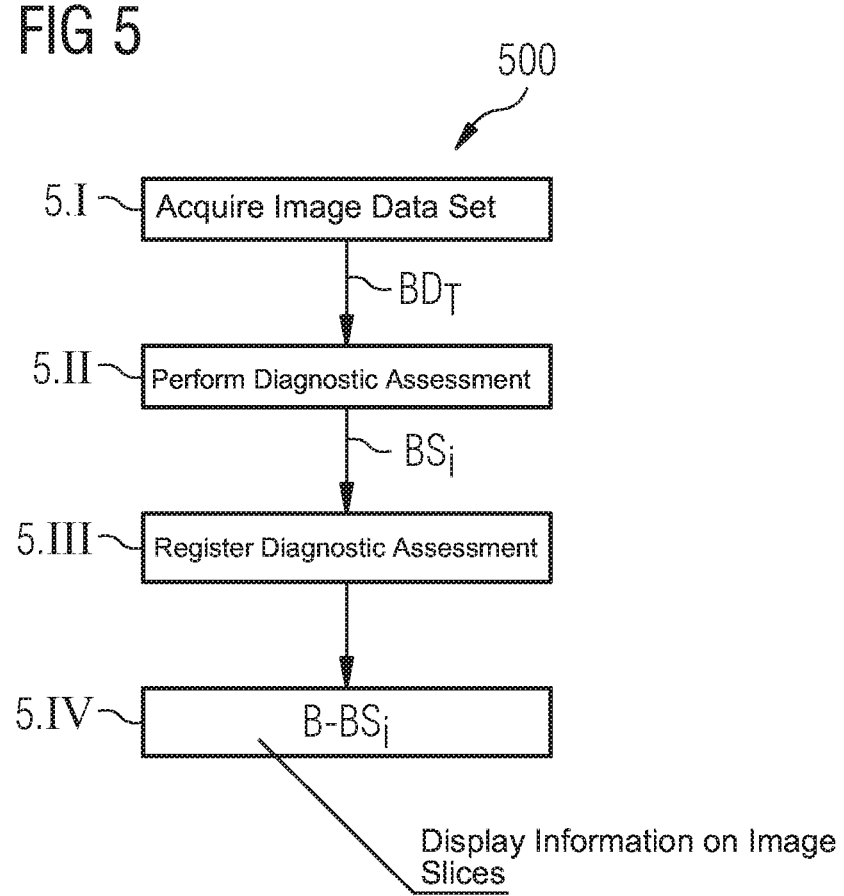

METHOD AND DEVICE FOR MONITORING A BREAST EXAMINATION

CROSS-REFERENCE TO RELATED APPLICATION

This application claims the priority, under 35 U.S.C. § 119, of German application DE 10 2016 208 647.2, filed May 19, 2016; the prior application is herewith incorporated by reference in its entirety.

BACKGROUND OF THE INVENTION

Field of the Invention

The invention relates to a method for monitoring a breast tissue examination. The invention furthermore relates to a method for diagnostic assessment of breast tissue that is to be examined. The invention also relates to an examination workflow monitoring device. The invention additionally relates to a diagnostic assessment station.

Procedures known as mammography screenings are carried out in many countries to provide early detection of breast cancer. Within the framework of the screening program it is sought to provide that the greatest possible number of women for whom breast cancer might pose a significant health risk routinely undergo a mammography examination at certain time intervals. Even today, very large volumes of data are collected in such a process. For example, four views of the female breast are typically produced in an examination of a single individual.

In conventional mammography, an x-ray projection image of the female breast is generated. The x-ray radiation used for this is a soft radiation having an energy of approximately 25 to 35 keV. In order to detect the x-rays, direct digital detectors and indirect digital detectors are employed to measure the emitted x-ray radiation. Direct digital detectors convert the x-ray radiation directly into an electrical signal. Indirect digital detectors, in contrast, firstly convert the x-ray radiation into visible light, which subsequently is converted into an electrical signal. The acquired x-ray projection images are viewed on a special mammography diagnostic assessment station which contains one or two grayscale monitors by which the x-ray projection images are visualized. An arrangement for two-dimensional mammography is shown in FIG. 1.

In traditional two-dimensional mammography there exists the problem that pathological changes in the tissue are often hidden due to the overlapping of different tissue structures, with the result that such changes are not detected. Attempts to compensate for this problem consist in acquiring images of the breast from two different angles, "craniocaudal" and "mediolateral oblique", i.e. one view is taken perpendicularly and one at a 45° angle thereto.

In order to improve early detection and diagnostic assessment, new and more effective examination methods beneficially find application also, such as tomosynthesis, for example.

Three-dimensional breast tomosynthesis provides an imaging method in which images of the breast are captured from many different angles. For example, images are acquired at angles of 15 to 50 degrees. In total, for example, between 9 and 25 images are obtained from different angles at low dose and at a high acceleration voltage, such that the overall dose is roughly equivalent to that of a conventional two-dimensional mammography image acquisition. Images for individual slices of the breast tissue are computed from the acquired projection data. Typically, about ten slices are produced per centimeter of the compressed breast height, which therefore equates to up to one hundred slices in the case of large breast thicknesses. Filtered back projection is one example of a method that is employed in order to reconstruct a three-dimensional image of a region to be examined from the acquired projection data. The resulting three-dimensional image can be viewed slice by slice for diagnostic purposes. Because slices above and below the slice selected for viewing at any given time can be masked out during the diagnostic assessment, tissue changes are easier to detect. A system for three-dimensional imaging of breast tissue with the aid of tomosynthesis is shown in FIG. 2.

For diagnostic assessment of findings, a two-dimensional mammography image is also required in addition as a localizer or overview image. In the overview image, the physician preparing a set of diagnostic findings can mark specific regions that he or she causes to be displayed slice by slice in the acquired tomosynthesis images.

A medical image viewing management system which is configured to flag already viewed medical images is described in published, non-prosecuted German patent application DE 10 2006 000 713 A1, corresponding to U.S. Pat. No. 7,698,152.

In German utility model DE 20 2007 019 608 U1, the position and thickness of a currently viewed slice of a three-dimensional representation of medical image data in an imaged region are displayed.

Due to the large number of slices in the tomosynthesis images, there exists the problem that it is necessary for the diagnosis to evaluate an increased number of slice images and this requirement results in a manifold increase in the amount of work involved in reaching a diagnosis. There is therefore a need to limit the amount of effort expended in the examination of the breast tissue to a necessary minimum.

SUMMARY OF THE INVENTION

This object is achieved by means of a method for monitoring a breast tissue examination, a method for diagnostic assessment of breast tissue that is to be examined, an examination workflow monitoring device, and a diagnostic assessment station.

In the inventive method for monitoring a breast tissue examination, once a diagnostic assessment has been completed, individual image slices of a slice image dataset to be examined in respect of breast tissue that is to be examined are registered in an automated manner. What is to be understood as a diagnostic assessment in the present context is that a single image slice is called up by the user and is also presented pictorially to said user.

In addition, information relating to the already assessed and the not yet assessed image slices is automatically displayed to the user. In other words, the user receives information concerning which of the image slices of a slice image dataset have already been displayed to him or her and which have not yet been displayed to him or her. Advantageously, therefore, the user has an overview of the current status of his or her work at all times during the diagnostic assessment process and in particular can avoid an unintended repetition of a diagnostic assessment of an individual image slice, as a result of which the user can save both time and effort. Furthermore, the user has a means of checking that he or she has also evaluated all of the image slices and has not inadvertently omitted any image slices. In particular when different individuals work one after another on preparing diagnostic findings, they are able to keep informed about the work already carried out by colleagues and thus avoid both unnecessary redundancy and gaps in the diagnostic assessment. In this way, both the efficiency of the diagnostic assessment and its confidence level and reliability are increased.

In the inventive method for diagnostic assessment of breast tissue that is to be examined, a slice image dataset of the breast tissue to be examined is acquired. In addition, a diagnostic assessment is carried out on the basis of the slice image dataset, wherein individual image slices of the slice image dataset are evaluated. Furthermore, an inventive method for monitoring a breast tissue examination is carried out.

Within the scope of the monitoring of the breast tissue examination, the respective status of the examination is communicated to the personnel conducting the examination in order to ensure an effective and complete evaluation of the breast tissue that is to be examined.

The inventive examination workflow monitoring device has a registration unit for automated registration of a completed diagnostic assessment of individual image slices. What is to be understood by "registration" in this context is the determining and recording of a completed diagnostic assessment. Thus, if an image slice is called up, it is also established at the same time that the image slice is assessed. In addition, this information is also stored so that the information will be permanently available to the user. The inventive examination workflow monitoring device additionally contains an image slice information display unit for the automated displaying of information relating to the already assessed and the not yet assessed image slices. In other words, information concerning which image slices have already been retrieved and which have not yet been retrieved is displayed to the user, thus enabling the user to concentrate on the slices that have not yet been assessed.

The inventive diagnostic assessment station has an input interface for acquiring a slice image dataset of the breast tissue that is to be examined. In addition, the inventive diagnostic assessment station contains a diagnostic assessment unit for carrying out a diagnostic assessment of findings on the basis of the slice image dataset, wherein individual image slices of the slice image dataset are displayed for evaluation. The inventive diagnostic assessment station also has an inventive examination workflow monitoring device.

Most of the essential components of the inventive examination workflow monitoring device and the inventive diagnostic assessment station can be embodied in the form of software components. This relates in particular to the registration unit, the image slice information display unit and the diagnostic assessment unit. In principle, however, some of these components can also be realized in the form of software-assisted hardware, for example field programmable gate arrays (FPGAs) or the like, in particular when there is a requirement for particularly fast calculations. Equally, the required interfaces can be embodied as software interfaces, for example when it is simply a matter of importing data from other software components. They can, however, also be embodied as hardware-based interfaces which are controlled by suitable software.

A largely software-based implementation has the advantage that diagnostic assessment stations already used previously in the prior art can also be easily upgraded by means of a software update in order to operate in the manner according to the invention. In that respect the object is also achieved by a corresponding computer program product having a computer program which can be loaded directly into a memory device of an inventive diagnostic assessment station, having program sections for the purpose of carrying out all steps of the inventive method when the computer program is executed in the diagnostic assessment station.

As well as the computer program, such a computer program product may also contain additional constituent parts such as e.g. documentation and/or additional components, including hardware components, such as e.g. hardware keys (dongles, etc.) to allow use of the software.

A computer-readable medium, for example a memory stick, a hard disk or some other transportable or permanently installed data carrier, on which the program sections of the computer program that can be read in and executed by a computer unit of the diagnostic assessment station are stored, may be used for transporting the computer program to the memory device of the diagnostic assessment station and/or for storing the same on the diagnostic assessment station. For this purpose, the computer unit may have e.g. one or more cooperating microprocessors or the like.

The dependent claims as well as the following description in each case contain particularly advantageous embodiments and developments of the invention. In this regard, in particular the claims of one claims category may also be developed analogously to the dependent claims of a different claims category. Furthermore, the various features of different exemplary embodiments and claims may also be combined within the scope of the invention in order to create new exemplary embodiments.

In an embodiment of the inventive method for monitoring a breast tissue examination, the slice image dataset contains a 3D mammography image dataset, preferably a tomosynthesis image dataset. In a 3D mammography procedure, a slice image dataset is generated in order to enable more effective identification of individual regions in the breast tissue, wherein an expert evaluator is able to view the individual image slices and in this way more accurately detect structures that would have been concealed in a 2D image. One possibility of obtaining such a 3D slice image dataset is the already mentioned tomosynthesis. By virtue of the 3D visualization, the expert evaluator is advantageously afforded the possibility of conducting a detailed examination of the breast region in all three dimensions, without individual structures obscuring or overlapping one another. To that end, the expert evaluator must scroll through the 3D images slice by slice in the search for conspicuous structures, such as lesions, for example. With the aid of the inventive method, the user is afforded the possibility of having the procedural steps taken in his or her evaluation of the individual image slices recorded automatically and as a result is able to monitor and control the evaluation at all times. In particular, he or she can thus avoid unwanted redundancy during the examination and so save time and effort.

In a preferred embodiment of the inventive method for monitoring a breast tissue examination, the already assessed and the not yet assessed image slices are displayed by an additional display field. What is to be understood as an additional display field in the present context is an area on a graphical display, for example a screen, which is displayed in addition to a display area which visualizes the image slices of the 3D slice image dataset. Such a display field may include for example an indicator bar by which not yet assessed image slices are flagged with a different marking than already assessed image slices. In this way the user is afforded the possibility of surveying at a glance which image slices he or she has already processed and which he or she still has to examine.

In addition, a slice position of an image slice currently being assessed can be automatically displayed to the user in the indicator bar, i.e. a section of the indicator bar symbolizing the image slice currently being assessed is flagged by means of a special marking when a desired slice is retrieved. For example, the section is given a colored border so that the user knows at which position in the breast to be examined he or she is currently situated in the slice direction or at which position the image slice currently being examined is located. Advantageously, the user can selectively view individual slices and at any given time knows the current position of the viewed slice in the slice stack.

It is particularly preferred if, within the scope of the inventive method for monitoring a breast tissue examination, a desired image slice is selected in the indicator bar. In other words, the indicator bar not only serves for displaying individual, already assessed image slices and their position in the slice direction, but in addition the indicator bar also has a selection function which consists in enabling individual sections of the indicator bar which symbolize individual image slices to be selected, and as a result an associated image slice is selected and automatically displayed for diagnostic assessment on a screen or display field of the screen. In this way the user is advantageously able to navigate between different image slices with the aid of the indicator bar and have the slices displayed to him or her. In this special embodiment, the additional display field therefore has a navigation function.

In a variant of the inventive method for monitoring a breast tissue examination, which variant is to be applied particularly advantageously, the navigation function is triggered by selecting a region associated with an image slice in the display field and automatically displaying the image slice associated with the selected region. The region associated with an image slice can preferably be a section of an indicator bar which can be selected by the user in the manner already described and the selection of which is accompanied by an automatic display of the image slice associated with said section.

Within the scope of a preferred variant of the inventive method for diagnostic assessment of breast tissue that is to be examined, it is possible in addition to generate an overview image dataset or to use an overview image dataset which was already generated during the x-ray projection image acquisition and supplied together with the slice image dataset and contains an overview image representation of the breast tissue that is to be examined. The overview image can be for example a two-dimensional mammography image which preferably represents a projection of the breast to be examined in the slice direction. The overview image dataset and an individual slice of the slice image dataset are displayed concurrently. In this case the user can select individual regions in the overview image and have these displayed for his or her perusal in a slice image. In other words, an image slice to be evaluated from the slice image dataset is selected by focusing in on a region of interest in the overview image. For this purpose it is computationally determined, on the basis of the selected two-dimensional region of interest, at which position in the slice direction the structures visible in the region of interest are located. In this case it is also possible to determine a plurality of image slices or image slice sequences which are adjacent to one another or also which are at a distance from one another or, as the case may be, which are separated from one another by other image slices and displayed one by one to the user. In addition, within the scope of a particularly preferred variant of the inventive method for the diagnostic assessment of breast tissue that is to be examined, the region of interest selected in the overview image is also marked, and hence displayed, in the respective determined and displayed image slices. Accordingly, the view of the observer during the evaluation of the individual image slices is immediately directed to the region that he or she has selected in the visualization of the individual image slices, which makes it easier for the user to conduct a diagnostic assessment and saves him or her from spending time unnecessarily in searching for the region of interest in the respective image slice.

In a particularly advantageous embodiment of the inventive method for the diagnostic assessment of breast tissue that is to be examined, the image slice to be evaluated is selected, preferably in an automated manner, as a function of the position in the slice direction of a tissue structure visualized in the region of interest. In other words, the position and the extent of the tissue structure in question in the slice direction are determined and the image slice participating at said position or extent is selected and displayed to the user.

Other features which are considered as characteristic for the invention are set forth in the appended claims.

Although the invention is illustrated and described herein as embodied in a method and a device for monitoring a breast examination, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 5 is a flowchart which illustrates a method for diagnostic assessment of breast tissue that is to be examined according to an exemplary embodiment of the invention.

DETAILED DESCRIPTION OF THE INVENTION

Figure 1:
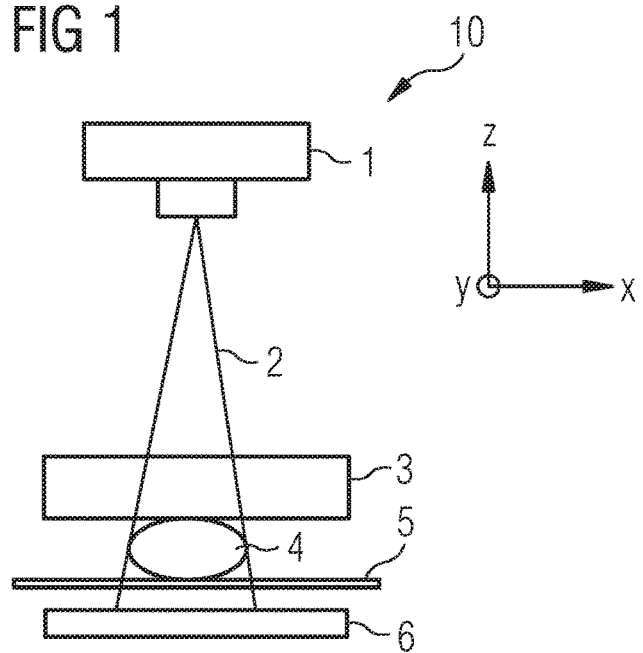
FIG. 1 is an illustration of a mammography system for two-dimensional x-ray imaging of a breast.

Referring now to the figures of the drawings in detail and first, particularly to FIG. 1 thereof, there is shown a system 10 for two-dimensional x-ray imaging of the breast, also known as a mammography system. The mammography system 10 contains an x-ray source 1 from which x-ray radiation 2 is emitted in a fan-shaped beam, i.e. in a beam opening out orthogonally to the propagation direction, in the direction of a breast 4. The breast 4 is positioned on a breast support table 5 and is pressed against the breast support table 5 by a compression paddle 3. In this way the thickness of the breast 4 is reduced in the propagation direction of the x-ray radiation 2, i.e. in the z-direction. The reduction in the thickness of the object 4 irradiated by the x-ray radiation 2 is accompanied by a decrease in the scattered radiation. Some of the x-ray radiation 2 incident on the breast 4 is absorbed. The rest of the x-ray radiation 2 incident on the breast 4 is transmitted and detected by an image sensor 6, in this case an x-ray detector.

Figure 2:
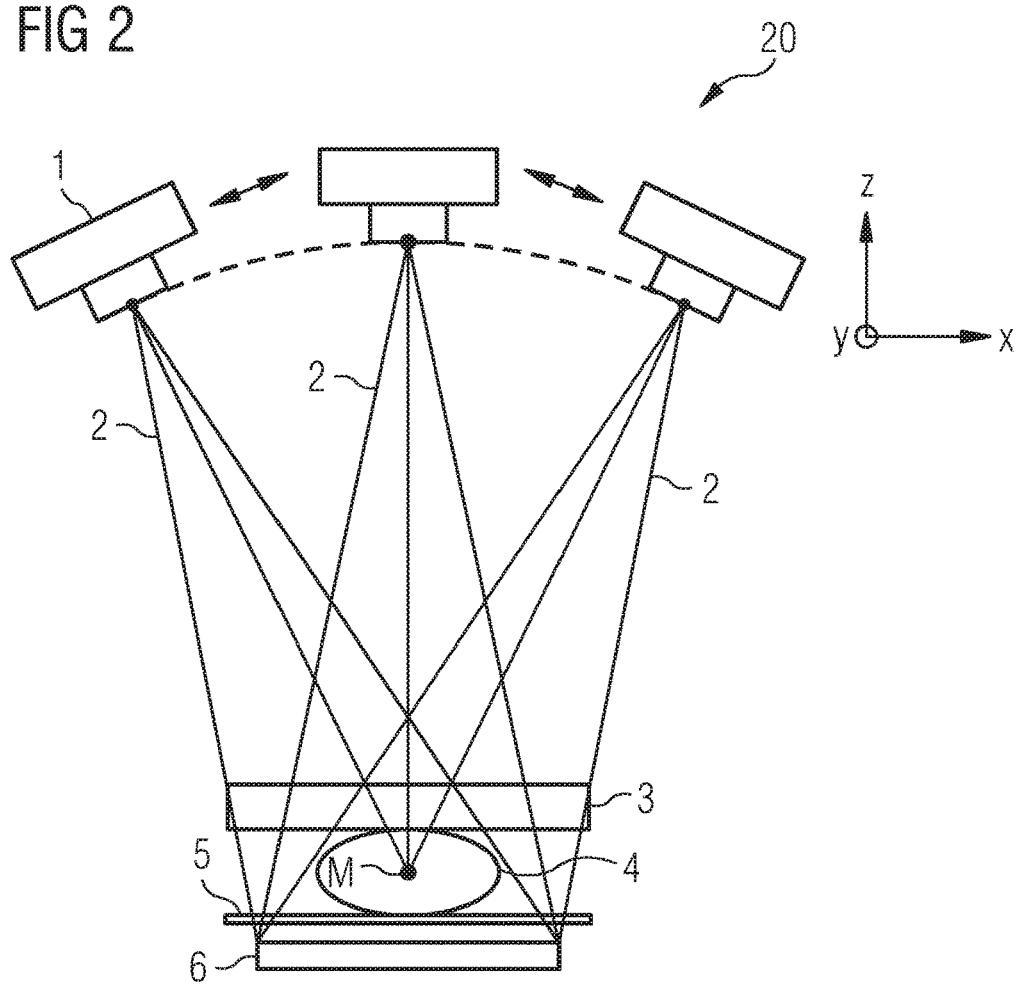
FIG. 2 is an illustration of a tomosynthesis system for three-dimensional x-ray imaging of a breast.

A conventional tomosynthesis system 20 for three-dimensional x-ray imaging of a breast 4 is shown schematically in FIG. 2. In contrast to the 2D mammography system 10 shown in FIG. 1, the tomosynthesis system 20 contains an x-ray source 1 which is rotatable around the object center point M and by which x-ray imaging of a breast 4 can be performed from different directions or angles. The tomosynthesis system 20 shown in FIG. 2 also contains a compression paddle 3 which presses the breast 4 to be examined against a breast support table 5. The breast 4 to be examined is irradiated by the x-ray source 1 from different angles, during which process a plurality of individual images of the breast 4 are acquired by an x-ray detector 6, also known as an image sensor. A three-dimensional slice image representation is calculated from the individual images, thus enabling a slice-by-slice examination of the tissue of the imaged breast 4.

Figure 3:
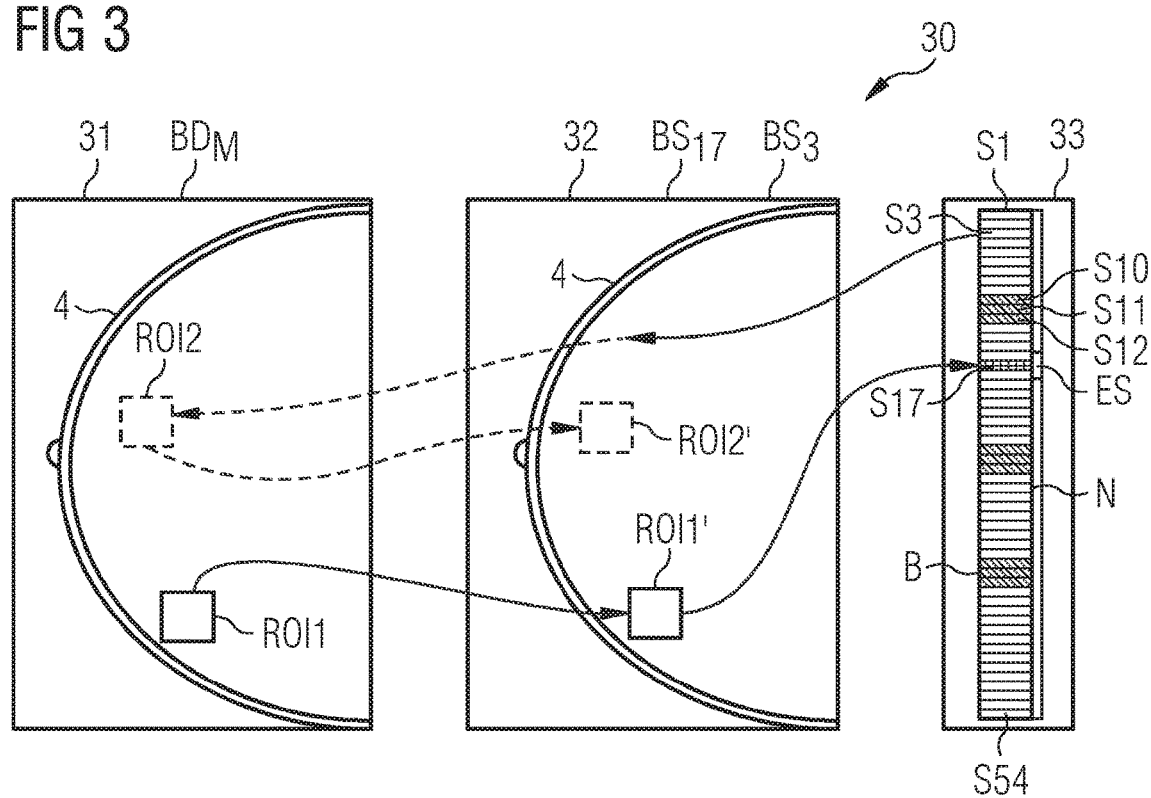
FIG. 3 is an illustration of a concurrent display of a slice image and an overview image and in addition an indicator bar which provides information concerning the already processed image slices and the still to be processed image slices within the scope of a diagnostic assessment, according to an exemplary embodiment of the invention.
Figure 4:
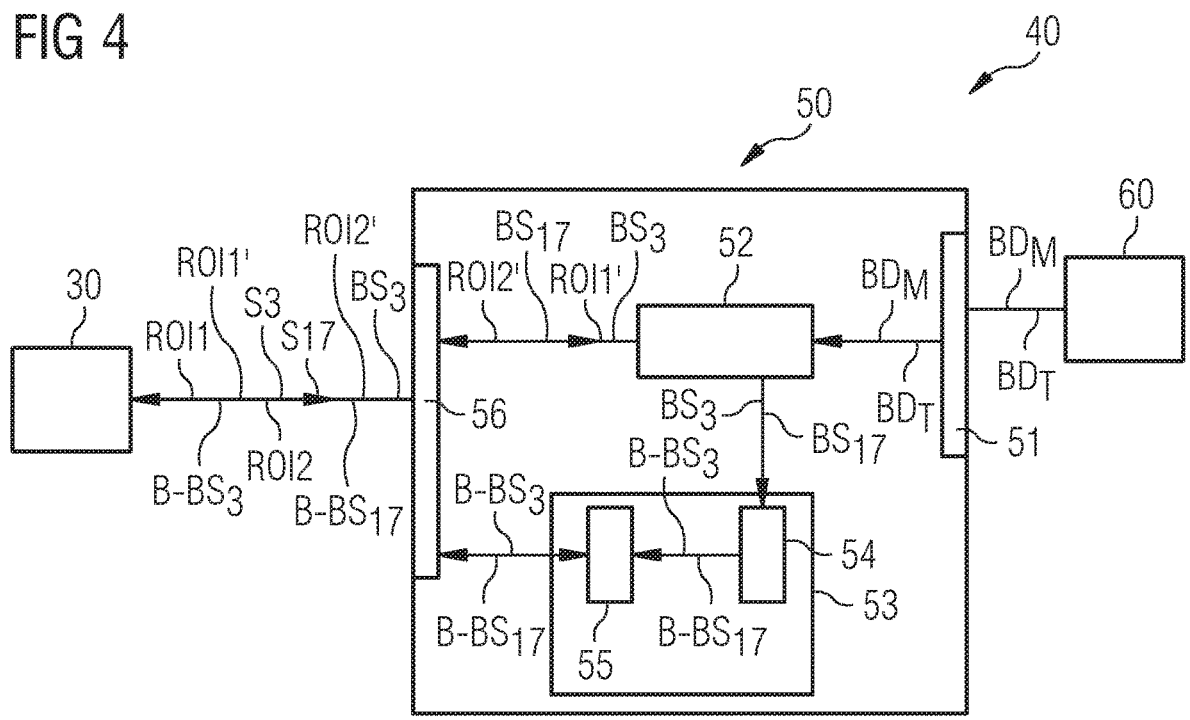
FIG. 4 is a block diagram which shows a breast examination system having a diagnostic assessment station according to an exemplary embodiment of the invention.

FIG. 3 shows a graphical user interface 30 of a diagnostic assessment station (see FIG. 4). The graphical user interface 30 may be embodied for example in the form of a screen, implemented as a touchscreen, or in the form of a combination of a screen with an input unit, such as a mouse or a keyboard, for example. Mammographic image data of the diagnostic assessment station is shown on the screen. Furthermore, instructions to the diagnostic assessment station may also be input via the graphical user interface 30 in order, for example, to display specific image slices containing the mammographic image data. A two-dimensional overview image $BD_M$ of a female breast 4 viewed from above is shown in a left-hand subarea 31 on a display field of the graphical user interface 30. A slice-by-slice visualization of the female breast 4 viewed from above is shown in a central subarea 32. A navigation aid in the form of an indicator bar B is also shown in a right-hand subarea 33. In the present example, the indicator bar B has a plurality of fifty-four slice fields S1, . . . , S54 in total, each of which is associated with an acquired image slice $BS_i$, which can be displayed in the central subarea 32. The indicator bar B additionally contains a navigation bar N with a slider element ES which can be moved to any desired slice field position S1, . . . , S54 in order to display a corresponding image slice BS; in the central subarea 32. The individual image slices BS; can therefore be selected and called up with the aid of the slider element ES in order to be displayed in the central subarea 32. According to an exemplary embodiment of the inventive method for monitoring a breast tissue examination, the already retrieved image slices or the slice field positions S10, S11, S12 associated therewith are colored green, which is indicated in FIG. 3 by means of oblique hatching.

The slices not yet retrieved or their associated slice field positions are colored red, which is indicated in FIG. 3 by means of an absence of hatching of the corresponding areas of the indicator bar B. The slice field position S17 of the indicator bar B associated with the image slice $BS_{17}$ just retrieved is flagged by a special marking, for example by a different color or colored border, which is symbolized in FIG. 3 by checkered hatching. The checking and display of the image slices read or not read in each case results in a kind of progress indicator. In addition, the radiologist preparing the diagnostic findings can selectively call up the image slices that have not yet been viewed, thereby avoiding certain image slices from being inspected twice and others in turn not being examined at all. A further function of the exemplary embodiment shown in FIG. 3 consists in being able to store information relating to the viewed image slices, for example with regard to provisional diagnostic findings, in the supplementary information thereof in order in this way to be able subsequently to track the progress of the diagnostic assessment and in order to obtain information for further optimizations of the diagnostic assessment.

A further feature of the embodiment variant shown in FIG. 3 is that in the left-hand subarea 31 in the overview image a first region of interest ROI1, which is flagged by a rectangular marking in the bottom left subarea 31, can be selected. Then, depending on in which slice the structures present in the region of interest ROI1 are mainly located, the corresponding image slice for the first region of interest ROI1 is automatically displayed in the central subarea 32, wherein the position or, as the case may be, a region ROI1' corresponding to the first region of interest ROI1 is also simultaneously transferred onto the image slice $BS_{17}$ that is to be displayed and is also displayed in the central subarea 32 at the cited position. This process is symbolized in FIG. 3 by a solid arrow between the first region of interest ROI1 and the region ROI1' corresponding thereto in the associated image slice $BS_{17}$.

Dashed arrows indicate the process sequence for selecting an image slice $BS_3$ with the aid of the indicator bar B, wherein an image slice field S3 corresponding to the desired image slice $BS_3$ is first selected on the indicator bar B with the aid of the slider element ES. The corresponding slice is then displayed on the screen in the central subarea 32. Following this, a second region of interest ROI2 is flagged by the user with an additional marking in the left-hand subarea 31 of the display 30. The second region of interest ROI2 is subsequently transferred automatically into the third image slice $BS_3$ displayed in the central subarea 32 and corresponding to the image slice field S3, where said region is designated as ROI2'.

FIG. 4 shows a breast examination system 40 having a diagnostic assessment device 50, also known as a diagnostic assessment station, according to an exemplary embodiment of the invention. The breast examination system 40 additionally has a medical imaging device 60 by which both an overview image of a breast that is to be examined is acquired, for example as a 2D mammography image $BD_M$, and in addition a three-dimensional image $BD_T$, for example a tomosynthesis image, of the breast that is to be examined is acquired. Furthermore, the breast examination system 40 also contains the graphical user interface 30 illustrated in FIG. 3 in the form of a touch screen for communication with a user, for example a physician, who wishes to prepare a set of diagnostic findings on the basis of the acquired image data $BD_M$, $BD_T$. The image data $BD_M$, $BD_T$ acquired in relation to the breast to be examined on the part of the medical imaging device 60 is transmitted via an input interface 51 to the cited diagnostic assessment device 50. There, the image data $BD_M$, $BD_T$ is transmitted to a diagnostic assessment unit 52. The diagnostic assessment unit 52 is configured to select individual image slices $BS_i$ (in this case the image slices $BS_3$, $BS_{17}$) of the three-dimensional image data $BD_T$ and to display the same concurrently with the overview image data $BD_M$ on the graphical interface 30. The diagnostic assessment unit 52 is furthermore configured to localize, on the basis of a region of interest ROI1 specified by the user, a tissue structure present in the region ROI1 and to select an image slice $BS_{17}$ associated with one or more of the tissue structures and to display the same on the screen 30 by transmission via an output interface 56. In addition, a region ROI1' corresponding to the position of the region of interest ROI1 is also displayed together with the respective image slice $BS_{17}$.

The diagnostic assessment unit 52 furthermore passes on the information relating to the selected or identified image slice $BS_{17}$ to an examination workflow monitoring device 53. The examination workflow monitoring device 53 contains a registration unit 54 and an image slice information display unit 55. On the basis of the information obtained in relation to the displayed image slice $BS_{17}$, the registration unit 54 registers and stores information to the effect that said image slice $BS_{17}$ is currently undergoing a diagnostic assessment. It then forwards the information B-$BS_{17}$ to the image slice information display unit 55, which outputs an instruction to present the information B-$BS_{17}$ on the screen 30 via the output interface 56 to the effect that the image slice $BS_{17}$ in question is currently being assessed. This information B-$BS_{17}$ is displayed on the screen 30 for example by marking a section S17 associated with the image slice $BS_{17}$ on an indicator bar B (see FIG. 3).

Conversely, an image slice $BS_3$ that is to be displayed on the screen 30 can also be selected directly by a user in that, for example, the user moves a slider element ES on a navigation bar N to the desired position S3 (see FIG. 3). In the case of a touch-screen being used, for example, the information concerning the selected area S3 of the indicator bar B associated with a specific slice $BS_3$, as well as a region of interest ROI2 possibly selected on the overview image, is transmitted via the input/output interface 56 to the diagnostic assessment unit 52. In the diagnostic assessment unit, a desired image slice $BS_3$ and a region of interest ROI2' corresponding to the selected region of interest ROI2 are determined in the selected image slice $BS_3$ and displayed on the screen 30 via the input/output interface 56. In addition, the information concerning the selected image slice $BS_3$ is passed on to the examination workflow monitoring device 53 or, as the case may be, to the registration unit 54 integrated therein. The registration unit 54 stores the information B-$BS_3$ to the effect that the image slice $BS_3$ in question is currently being assessed and forwards said information B-$BS_3$ to the image slice information display unit 55. The image slice information display unit 55 transmits, via the input/output interface 56, an instruction to display information B-$BS_3$ on the screen 30 indicating that the image slice $BS_3$ in question is currently being assessed. This information is displayed on the screen 30 for example by marking a section S3 associated with the image slice $BS_3$ on an indicator bar B (see FIG. 3).

FIG. 5 shows a flowchart 500 by which a method for diagnostic assessment of breast tissue that is to be examined is illustrated. Firstly, at a step 5.I, a slice image dataset $BD_T$ of the breast tissue 4 to be examined is acquired. The slice image dataset $BD_T$ can be acquired for example with the aid of a tomosynthesis imaging method. Next, at step 5.II, a diagnostic assessment is carried out on the basis of the slice image dataset $BD_T$, wherein individual image slices $BS_i$ of the slice image dataset $BD_T$ are evaluated.

At step 5.III, the diagnostic assessment is now monitored in that a completed diagnostic assessment of individual image slices $BS_i$ of a slice image dataset $BD_T$ to be examined in respect of breast tissue that is to be examined is registered in an automated manner. In addition, at step 5.IV, information B-$BS_i$ relating to the already assessed and the not yet assessed image slices is automatically displayed so that a user can selectively pick out the not yet assessed slices and document his or her work and can thus avoid unnecessary additional effort, in particular due to an unintended duplicated diagnostic assessment of individual slices.

In conclusion, it is pointed out once again that the methods and devices described in the foregoing are simply preferred exemplary embodiments of the invention and that the invention may be varied by the person skilled in the art without departing from the scope of protection of the invention insofar as this is defined by the claims. Accordingly, the method for diagnostic assessment of breast tissue that is to be examined and the examination workflow monitoring device 53 have been illustrated primarily on the basis of the visualization of tomosynthesis image data $BD_T$. However, the invention is not limited to an application to image data of said type, but rather the invention may also be applied generally to all types of slice image visualizations. It is also pointed out for the sake of completeness that the use of the indefinite articles "a" or "an" does not exclude the possibility that the features in question may also be present more than once. Equally, the term "unit" does not rule out the possibility that the same consists of a plurality of components, which if necessary may also be spatially distributed.

The following is a summary list of reference numerals and the corresponding structure used in the above description of the invention:

1 X-ray source 1
2 X-ray radiation
3 Compression plate
4 Breast
5 Breast support table
6 Image sensor/x-ray detector
10 Mammography system
20 Tomosynthesis system
30 Graphical user interface/display
31 Left subarea
32 Central subarea
33 Right subarea
40 Breast examination system
50 Diagnostic assessment device/diagnostic assessment station
51 Input interface
52 Diagnostic assessment unit
53 Examination workflow monitoring device
54 Registration unit
55 Image slice information display unit
56 Output interface
60 Medical imaging device
B Indicator bar
B-$BS_i$, B-$BS_3$, B-$BS_{17}$ Information concerning assessed image slice
$BD_M$ 2D mammography image
$BD_T$ Three-dimensional image acquisition
$BS_i$, $BS_3$, $BS_{17}$ Image slice
ES Slider element
M Object center point
N Navigation bar
ROI1 First region of interest
ROI1' Region corresponding to the first region of interest ROI2 Second region of interest
ROI2' Region corresponding to the second region of interest
S1, . . . , S54 Slice fields/slice field positions
S3, S10, S11, S12, S17 Slice field positions

The invention claimed is:

1. The method for monitoring a breast tissue examination, which comprises the steps of:
providing an imaging machine having an emitting source and a detector;
generating a slice image dataset with the imaging machine, wherein the imaging machine uses the emitting source and the detector for creating the slice image dataset;
performing an automated registration of a completed diagnostic assessment of individual image slices of the slice image dataset to be examined in respect of breast tissue that is to be examined; and
continuously displaying information relating to a status of all the individual image slices of the slice image dataset as being either a completed diagnostic assessed image slice or a not yet completed diagnostic assessed image slice while a user is performing a diagnosis of the individual image slices so that the user can selectively pick out not yet completed diagnostic assessed image slices to be viewed next, the information being displayed on an additional display field separate from a display field of the individual image slices.

2. The method according to claim 1, wherein the slice image dataset contains a 3D mammography image dataset.

3. The method according to claim 1, which further comprises displaying the information related to the completed diagnostic assessed image slices and the not yet completed diagnostic assessed image slices sequentially and directly adjacent to each other on the additional display field.

4. The method according to claim 3, wherein the additional display field has an indicator bar for only displaying the status of the individual image slices.

5. The method according to claim 4, wherein the indicator bar flags the not yet completed diagnostic assessed image slices with a different marking than the completed diagnostic assessed image slices.

6. The method according to claim 4, which further comprises performing at least one of:
automatically displaying a slice position of a currently assessed image slice in the indicator bar; or
selecting a desired image slice in the indicator bar and the slice is automatically displayed for diagnostic assessment.

7. The method according to claim 4, wherein the additional display field has a navigation function.

8. The method according to claim 7, wherein the navigation function is triggered by selecting a section associated with an image slice in the additional display field and the image slice associated with a selected section is displayed automatically.

9. The method according to claim 2, wherein the 3D mammography image dataset is a tomosynthesis image dataset.

10. The method according to claim 1, wherein the slice image dataset contains a tomosynthesis image dataset.

11. A method for diagnostic assessment of breast tissue that is to be examined, which comprises the steps of:
providing an imaging machine having an emitting source and a detector;
acquiring a slice image dataset of the breast tissue that is to be examined via the imaging machine, wherein the imaging machine uses the emitting source and the detector for creating the slice image dataset;
carrying out a diagnostic assessment on a basis of the slice image dataset, wherein individual image slices of the slice image dataset are evaluated;
performing an automated registration of a completed diagnostic assessment of the individual image slices of the slice image dataset to be examined in respect of the breast tissue that is to be examined; and
continuously displaying information relating to a status of all the individual image slices of the slice image dataset as being either a completed diagnostic assessed image slice or a not yet completed diagnostic assessed image slice while a user is performing a diagnosis of the individual image slices so that the user can selectively pick out not yet completed diagnostic assessed image slices to be viewed next, the information being displayed on an additional display field separate from a display field of the individual image slices.

12. The method according to claim 11, which further comprises:
acquiring an overview image dataset having an overview image of the breast tissue that is to be examined;
displaying the overview image dataset and an individual slice of the slice image dataset concurrently; and
selecting the image slice to be evaluated from the slice image dataset by focusing in on a region of interest in the overview image.

13. The method according to claim 12, which further comprises selecting the image slice to be evaluated, in an automated manner, in dependence on a position in a slice direction of a tissue structure visualized in the region of interest.

14. A diagnostic assessment station, comprising:
an imaging machine having an emitting source and a detector, said imaging machine uses said emitting source and said detector for creating a slice image dataset of breast tissue;
an input interface for acquisition of the slice image dataset that is to be examined from said imaging machine;
a diagnostic assessment unit for carrying out a diagnostic assessment on a basis of the slice image dataset, wherein individual image slices of the slice image dataset are displayed for evaluation;
an examination workflow monitoring device having a registration unit for automated registration of a completed diagnostic assessment of the individual image slices; and
an image slice information display unit for continuously displaying of information relating to a status of all the individual image slices of the image slice dataset as being either a completed diagnostic assessed image slice and not yet completed diagnostic assessed image slice while a user is performing a diagnosis of the individual image slices so that the user can selectively pick out the not yet completed diagnostic assessed image slices to be viewed next, the information being displayed on a display field separate from a display field of the individual image slices.

15. A non-transitory computer-readable medium having computer-executable instructions which can be read in and executed by a processor of a computer for performing a method for monitoring a breast tissue examination, which comprises the steps of:
powering up an imaging machine having an emitting source and a detector;

generating a slice image dataset with the imaging machine, wherein the imaging machine uses the emitting source and the detector for creating the slice image dataset;

performing an automated registration of a completed diagnostic assessment of individual image slices of the slice image dataset to be examined in respect of breast tissue that is to be examined; and continuously displaying information relating to a status of all the individual image slices of the image slice dataset as being either a completed diagnostic assessed image slice or a not yet completed diagnostic assessed image slice while a user is performing a diagnosis of the individual image slices so that the user can selectively pick out not yet completed diagnostic assessed image slices to be viewed next, the information being displayed on a display field separate from a display field of the individual image slices.

* * * * *